United States Patent [19]

Iannone

[11] Patent Number: 5,343,882
[45] Date of Patent: Sep. 6, 1994

[54] FOOT CARE KIT

[76] Inventor: Sam Iannone, 15 W. Willow St., Beacon, N.Y. 12508

[21] Appl. No.: 72,098

[22] Filed: Jun. 7, 1993

[51] Int. Cl.⁵ .................................................. A45D 33/26
[52] U.S. Cl. ................................... 132/294; 132/286; 132/293; 132/299; 604/293
[58] Field of Search ............... 132/73, 73.5, 286, 293, 132/294, 298, 299, 307, 312, 313, 314, 315; 604/289, 290, 293

[56] References Cited

U.S. PATENT DOCUMENTS

| | | | |
|---|---|---|---|
| 1,025,924 | 5/1912 | Pike | 132/299 |
| 1,992,648 | 2/1935 | Browne | 604/293 |
| 2,061,142 | 11/1936 | Denocenzo . | |
| 2,321,807 | 6/1943 | Glickman . | |
| 2,389,788 | 11/1945 | Lathrop . | |
| 2,451,906 | 10/1948 | Berman | 604/293 |
| 2,594,024 | 4/1952 | Hyde | 604/293 |
| 3,130,726 | 4/1964 | Rich | 604/293 |
| 3,490,453 | 1/1970 | Ogden | 604/293 |
| 3,497,127 | 2/1970 | Box . | |
| 3,550,593 | 12/1970 | Kaufman | 604/293 |
| 3,664,353 | 5/1972 | Childress . | |
| 3,965,495 | 6/1976 | McNair . | |
| 4,005,531 | 2/1977 | Weintraub . | |
| 4,029,096 | 6/1977 | Fust | 604/293 |
| 4,075,457 | 2/1978 | Williams . | |
| 4,513,736 | 4/1985 | Thurber . | |
| 4,979,525 | 12/1990 | Chiou . | |
| 5,088,509 | 2/1992 | Savage . | |
| 5,095,924 | 3/1992 | Stanfield . | |

FOREIGN PATENT DOCUMENTS 0670199 10/1964 Italy ..................................... 604/293

Primary Examiner—Gene Mancene
Assistant Examiner—Frank A. LaViola
Attorney, Agent, or Firm—Terry M. Gernstein

[57] ABSTRACT

A kit includes a carrying case that has a powder absorbing mat fixed to an inner surface thereof. A plurality of foot-care accessories are also stored in the kit. The foot-care accessories include a flexible bag that is formed of material that will store medicated powder yet will dispense that powder on contact with a user's foot. The flexible bag is interdigitated between the user's toes and is attached to the foot. A user places his or her foot on either the mat or the flexible bag, scrapes or brushes the foot, and dusts the medicated powder onto the foot. Any powder that falls off is stored in the bag or the mat for application to the bottom of the user's foot. The bag is then applied to the foot if desired.

19 Claims, 2 Drawing Sheets

FOOT CARE KIT

TECHNICAL FIELD OF THE INVENTION

The present invention relates to the general art of personal hygiene, and to the particular field of foot care.

BACKGROUND OF THE INVENTION

Many people suffer various foot-related ailments. These ailments range in severity from minor irritations to major dermatological problems. By Ear the most common foot-related problem is a fungal infection commonly known as "athlete's foot." This infection is found in people of all ages and can encompass lo the same severity range as above mentioned for foot disorders in general.

The inventor has found that some fungus that is characterized as athlete's foot fungus thrives in damp or wet conditions. Therefore, if the damp or wet conditions are replaced by a dry environment, this particular fungus dies, thereby curing this form of athlete's foot.

The market contains several remedies directed to curing athlete's foot, including many forms of foot powder. While these powders and remedies are somewhat effective and have been fairly commercially successful, there is still room for improvement. Specifically, the inventor has found that these cures have several drawbacks. For example, some powders are messy to apply thereby discouraging their use, especially prolonged use as may be required to completely cure some forms of athlete's foot.

Still further, for those fungi that are most efficiently killed by maintaining a dry environment, such powders are only effective when they can absorb dampness. As soon as the powder falls off the user's skin, or absorbs all the moisture it is capable of absorbing, its effectiveness for those fungi will be minimized and possible non-existent.

Therefore, there is a need for a means and a method for applying powder to a user's foot in a manner that is not unduly messy yet will maintain as much effective powder as possible on the user's foot for as long as possible.

Yet another drawback to many presently-available foot powder-type remedies is the inaccuracy of the application thereof. Many foot fungal infections occur between the toes and/or between the toes and the front of the sole of the foot. It may be difficult for some people, especially elderly or overweight people, to place sufficient amounts of foot powder directly on the affected areas of their feet to be fully effective. Foot sprays are often inaccurate and can be extremely wasteful.

Therefore, there is a further need for a means and a method for applying powder-type medication to a user's foot accurately yet which easily and efficiently located the medication on the precise areas affected.

A still further drawback of many presently-available foot care remedies is that dead skin on the outer surface of the skin prevents the medication from reaching newly-affected areas by shielding those areas from the medication. Newly applied medication is simply applied to skin that no longer needs it. This is wasteful and inefficient.

Therefore, there is yet a further need for a means and a method for applying powder-type medication to a user's foot that prevents dead skin from interfering with contact between the medication and any fungus growing on the user's skin.

Still further, for many infections, several implements and accessories may be required to fully treat the affected area. This is especially true in the above-discussed situation where dead skin may prevent the medication from reaching newly-infected areas. If many such items are necessary, many users simply will not use all the items as it is inconvenient to carry them. This may reduce the effectiveness of any treatment.

Therefore, there is a need for a means and a method for applying powder-type medication to a user's foot in which all of the implements and accessories necessary for a complete treatment can be stored accessibly in a single case whereby a user can conveniently carry all these items for use when necessary.

OBJECTS OF THE INVENTION

It is a main object of the present invention to provide a means and a method for applying powder-type medication to a user's foot.

It is another object of the present invention to provide a means and a method for applying powder-type medication to a user's foot in all areas susceptible to fungal infections.

It is another object of the present invention to provide a means and a method for applying powder-type medication to a user's foot that can be used neatly, easily and accurately to apply medication to precisely those areas of a user's foot that are affected by a wetness-induced and sustained fungal infection.

It is another object of the present invention to provide a means and a method for applying powder-type medication to a user's foot which can maintain the medication in contact with the affected area for long periods.

It is another object of the present invention to provide a means and a method for applying powder-type medication to a user's foot which is not inhibited by the presence of dead skin in the infected area.

It is another object of the present invention to provide a means and a method for applying powder-type medication to a user's foot which can easily and effectively be applied between a user's toes and between those toes and the sole of the user's foot.

It is another object of the present invention to provide a means and a method for applying powder-type medication to a user's foot in which all necessary medications and/or implements necessary for a complete treatment can be stored in one convenient case.

It is another object of the present invention to provide a means and a method for applying powder-type medication to a user's foot which keeps waste to a minimum.

SUMMARY OF THE INVENTION

These, and other, objects are achieved by a kit that includes a briefcase-like housing in which a powder-absorbing mat is located along with a plurality of foot care items. The foot care items include medicated foot powder and a flexible bag that is formed of material that is porous to the medicated powder and which is interdigitated between a user's toes. The bag is attached to itself or to the user's foot to hold it in place on the user's foot. The kit also includes a brush for removing dead skin prior to application of the medicated powder. The powder is both medicated and moisture absorbing.

The kit is used by placing the user's foot on the mat and dusting powder onto the foot in the affected areas. Any powder that falls off the foot is adsorbed by the mat and is placed into contact with the bottom of the user's toes and/or foot the next time the user places his or her foot on the mat. Another way of using the kit is to place the bag on top of the mat, then place the foot on top of the bag, then dust the foot with the powder. The bag can also contain powder and can apply powder to the foot as well as catch powder that falls off the foot during the initial application step. The bag can then be interdigitated between the user's toes and attached to the user's foot to hold the bag in place with the medicated powder being applied to the user's foot. The bag thus keeps the user's foot and toes dry while maintaining the medicated powder in position to be applied to the affected areas for long periods.

The kit also includes a handled brush that is used to clean dead skin from the user's foot prior to applying the powder. The powder can be dusted onto the brush and applied using the brush if suitable.

In this manner, not only is medicated powder conserved, it is applied directly to the areas most in need of such application, it is maintained in contact with such areas long enough to keep them dry and to effect a cure. The overall process is effective yet is maintained neat and accurate and is desirable as all necessary accessories are in one location that can be conveniently moved from place to place and stored when not in use.

BRIEF DESCRIPTION OF THE DRAWING FIGURES

DETAILED DESCRIPTION OF THE PREFERRED EMBODIMENT OF THE INVENTION

Figure 1:
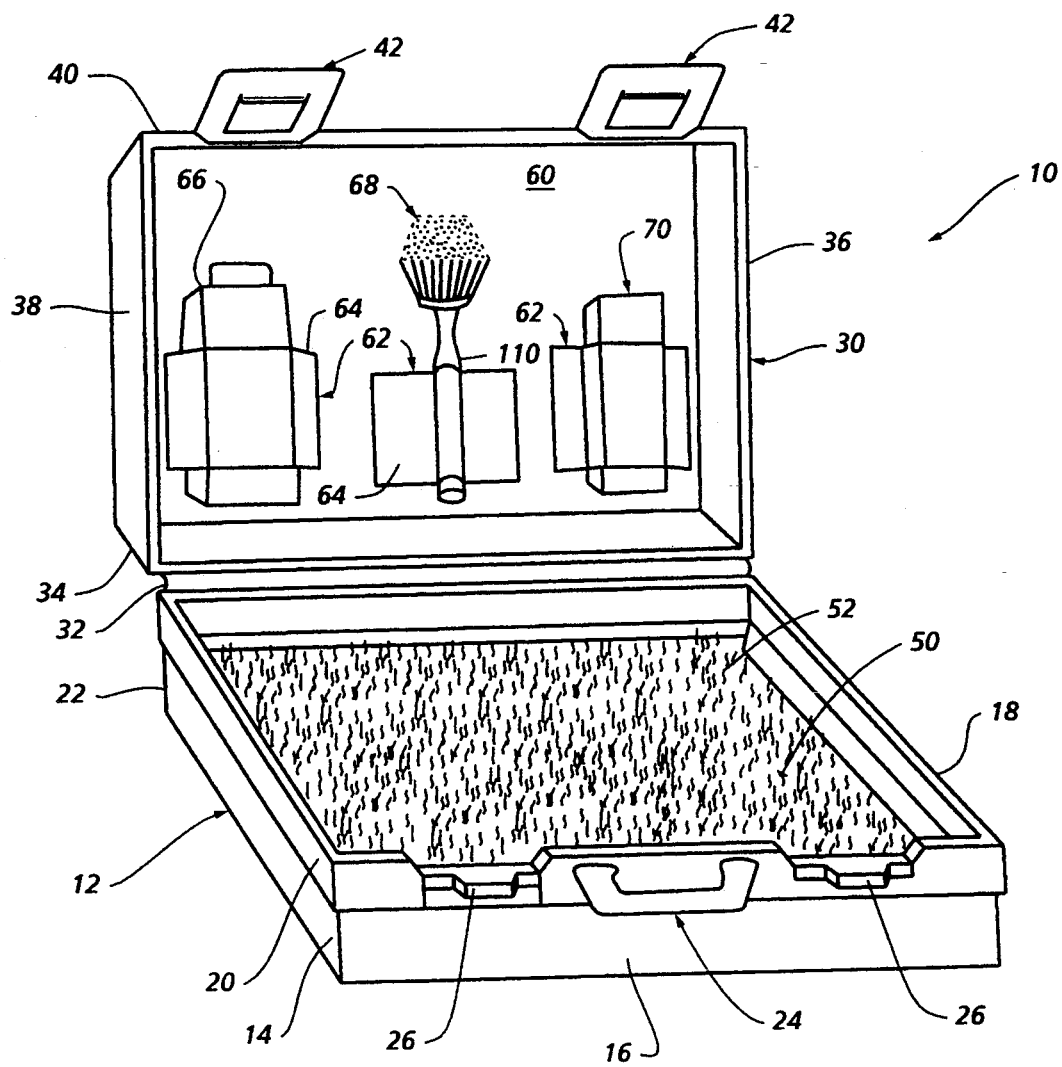
FIG. 1 is a is a front, top and end perspective view of the kit embodying the present invention with the case in the open condition.
Figure 2:
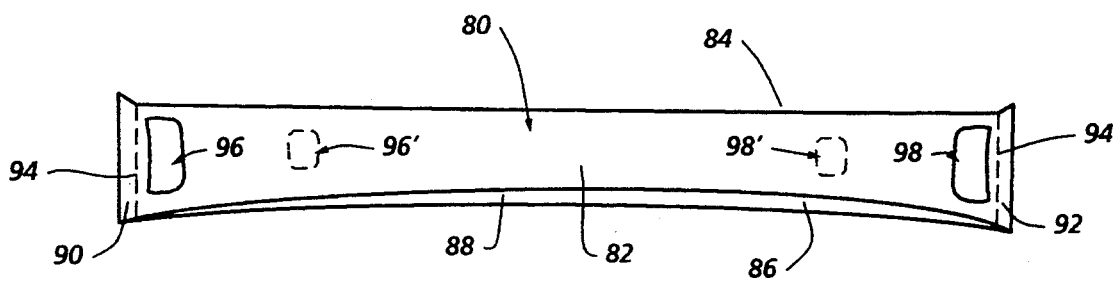
FIG. 2 is top and front perspective view of a bag used to apply medicated powder to a user's foot and/or toes.

Shown in FIG. 1 is a kit 10 which provides a means and is used in a method of applying medicated powder to a user's to cure and/or combat various foot-related ailments, such as athlete's foot or the like. Kit 10 includes a briefcase-like case 12 which keeps all of the accessories and implements in one convenient location that can be easily stored and moved about as desired. The case 12 includes a bottom section 14 having a front wall 16, side walls 18 and 20 and a rear wall 22. A carrying handle 24 is mounted on the front wall 16, as are lock elements 26. While a briefcase form of the case is shown, other forms of cases can be used without departing from the scope of this disclosure and the claims associated therewith.

Case 12 further includes a top section 30 attached to the bottom section rear wall by a hinge 32 connected to a rear wall 34 of the top section. The top section also includes side walls 36 and 38 and a front wall 40. Lock elements 42 are mounted on the front wall and cooperate with lock elements 26 to close the case and keep it closed.

Bottom section 12 includes an inner surface on which a mat 50 is mounted. The preferred form of mat 50 is a carpet-like material, but other similar materials can be used without departing from the scope of this disclosure and the claims presented herein, and variations will occur to one skilled in the art can understand from the teaching herein. Mat 50 has means, such as fibers 52, that adsorb and hold powder dropped thereon. However, such holding is not so secure that the powder cannot be wiped off onto a user's foot placed on top of the mat. Shag carpet is a suitable form of mat 50. Mat 50 is fixed to the bottom section.

Top section 30 includes an inner surface 60. A plurality of accessory mounts 62 are fixed to inner surface 60. Mounts 62 are shown as bands having ends 64 fixed to inner surface 60. In one form of the kit, inner surface 60 includes a hook-and-loop type fastening means, and bands 62 also include corresponding hook-and-loop fastening means whereby the bands can be mounted anywhere on inner surface 60 and any number of such bands can be used as desired. Three such bands are shown in FIG. 1 as an example.

Each of the accessory mounts stores a foot care item, such as a container of medicated powder 66, a handled-brush 68 and a package of toe-engaging bags 70. Other accessories will occur to one skilled in the art based on the teaching of this disclosure, and such accessories are intended to be included in the scope of this disclosure and claims as well.

A toe-engaging bag 80 is shown in FIG. 3. Bag 80 is formed of material that will hold powder commonly used to treat foot fungal infections such as athlete's foot, yet will be porous enough to permit that powder to pass into or out of the bag. Therefore, the bag has pores that are slightly larger than the grain size of such medicated powders. A preferred form of the bag material is cheese cloth. This material is flexible yet will function as above discussed to hold and dispense medicated powder for the purposes described herein. The bag includes a body 82 having sides 84 and 86 that are pleated at 88 so the bag can expand as necessary, and ends 90 and 92 that are stitched closed by stitching 94. Attaching elements 96 and 98 are located on the bag body adjacent to the stitching. The preferred form of attaching elements 96 and 98 is adhesive tape, but other forms of such elements can be used, including the above-mentioned hook-and-loop means as indicated at 96' and 98', as suitable. The bag is elongate and is long enough, as measured between ends 90 and 92, to perform the interdigitating feature discussed below.

Figure 3A:
FIGS. 3A-3E illustrate a method of applying the bag shown in FIG. 2 to a user's foot and/or toes.
Figure 3B:
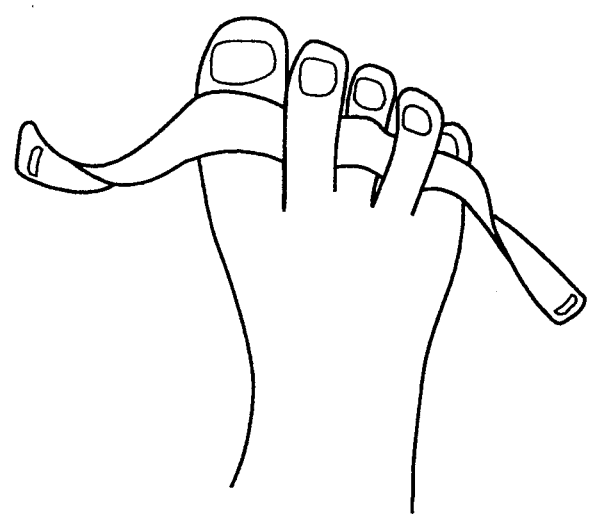
Figure 3C:
Figure 3D:
Figure 3E:
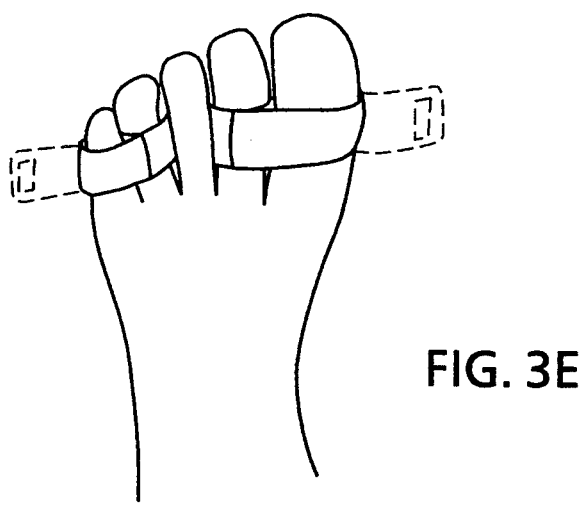

In use, bag 80 is interdigitated between a user's toes as shown in FIGS. 3A-3E. The bag is initially threaded between the toes as shown in FIG. 3A until it extends all the way across the user's foot as shown in FIG. 3B. The bag is then attached to the user's foot by winding the bag around the first and last toe on the user's foot and attaching elements 96 and 98 to the bag body as shown in FIGS. 3C-3E, with the unattached bag ends being indicated in dotted lines in FIG. 3E. The bag thus will be held in place on the user's foot for as long as desired. Any medication in the bag will be continuously applied to the user's foot when the bag is in the FIGS. 3D and 3E position. It is also noted that when the bag is applied as shown in FIGS. 3A-3E, it will scrape dead skin off the user's foot thereby improving the performance of the kit.

The foot care kit is used by placing the user's foot on mat 50, scraping the foot using brush 68 to remove dead skin, and dusting powder on the foot. The brush includes a handle 110, and handle 110 makes access to the user's foot easier, and can be any suitable length. Powder can be placed on bristle section 112 of the brush if desired. Any powder that falls off the foot is adsorbed in mat 50 and is then applied to the bottom of the user's foot the next time that foot is placed on the mat. Alternatively, a bag 80 can be placed on top of the mat before the user places his or her foot on the bag. Powder is then adsorbed by the bag or applied to the bottom of the foot if powder is stored in the bag. The bag is then interdigitated between the user's toes as above described in reference to FIGS. 3A–3E.

It is understood that while certain forms of the present invention have been illustrated and described herein, it is not to be limited to the specific forms or arrangements of parts described and shown.

I claim:

1. A foot care kit comprising:
   A) a case having a bottom section, a top section, a hinge connecting said top section to said bottom section, said bottom and said top sections each including an inner surface;
   B) a carrying handle on said case;
   C) lock means on said case for holding said top section to said bottom section;
   D) a porous, powder-absorbing mat fixed to said bottom section inner surface, said mat having a top surface and means for releasably holding powder on said top surface for retaining powder dropped on said mat when said case is moved and applying the powder to a user's foot that is placed on said said top surface;
   E) a plurality of accessory mounts on said top section inner surface, each of said accessory mounts including a strap;
   F) a plurality of foot-care accessories, each mounted in an accessory mount;
   means for releasably fixing said accessory mounts to said top section including hook-and-loop fasteners on said top section inner surface and covering a major portion of said top section inner surface and hook-and-loop fastener means on each of said straps whereby said straps can be placed and retained anywhere on said top section in any orientation.

2. The foot care kit defined in claim 1 wherein said mat includes a fiber carpet.

3. The foot care kit defined in claim 2 wherein said foot care accessories include a container of medicated powder, a handled brush, and a toe-engaging bag.

4. The foot care kit defined in claim 3 wherein said toe-engaging bag includes a flexible body having sides and ends and a length measured between said ends that exceeds a width thereof as measured between said sides, said body being formed of foraminous material having a pore size greater than the grain size of any powder used as medicated powder.

5. The foot care kit defined in claim 4 further including attaching means on said body adjacent to each of said ends.

6. The foot care kit defined in claim 5 further including medicated powder stored in said toe-engaging bag.

7. The foot care kit defined in claim 5 wherein said toe-engaging bag sides are pleated.

8. The foot care kit defined in claim 5 wherein said attaching means includes adhesive.

9. The foot care kit defined in claim 5 wherein said bag is formed of cheese cloth.

10. The foot care kit defined in claim 5 wherein said attaching means includes hook-and-loop fastening means.

11. A method of foot care comprising steps of:
    A) providing a container having a powder-retaining mat;
    B) placing a user's foot on the mat;
    C) placing foot-care powder on the user's foot;
    D) catching and retaining any powder than falls off the user's foot during said step of placing foot-care powder on the user's foot in the mat;
    E) applying powder to the bottom of the user's foot using the mat;
    G) interdigitating a flexible foot powder-containing flexible bag between all of the user's toes; and
    H) winding the flexible bag around the first and last toe of the user's foot and attaching the ends of the bag together to attach the flexible bag to the user's foot.

12. A foot care kit comprising:
    A) a case having a bottom section, a top section, a hinge connecting said top section to said bottom section, said bottom and said top sections each including an inner surface;
    B) a carrying handle on said case;
    C) lock means on said case for holding said top section to said bottom section;
    D) a porous, powder-absorbing mat fixed to said bottom section inner surface;
    E) a plurality of accessory mounts fixed to said top section inner surface;
    F) a plurality of foot-care accessories;
    G) a toe-engaging bag including a flexible body having sides and ends and a length measured between said ends that exceeds a width thereof as measured between said sides, said body being formed of foraminous material having a pore size greater than the grain size of any powder used as medicated powder, said toe-engaging bag being interdigitated between all of a user's toes and wound around the first toe and the last toe of the user's foot, means for releasably attaching each of said bag ends together, said bag ends being attached together at a location between said first and last toe, and medicated powder stored in said toe-engaging bag.

13. A foot care kit comprising:
    A) a case having a bottom section, a top section, a hinge connecting said top section to said bottom section, said bottom and said top sections each including an inner surface;
    B) a carrying handle on said case;
    C) a porous, powder-absorbing mat fixed to said bottom section inner surface;
    D) a plurality of accessory mounts fixed to said top section inner surface;
    E) a plurality of foot-care accessories including a toe-engaging bag including a flexible body having sides and ends and a length measured between said ends that exceeds a width thereof as measured between said sides, said body being formed of foraminous material having a pore size greater than the grain size of any powder used as medicated powder, said toe-engaging bag being interdigitated between all of a user's toes and wound around the first toe and the last toe of the user's foot, means for releasably attaching each of said bag ends together, said bag ends being attached together at a location between said first and last toe, and medicated powder stored in said toe-engaging bag.

14. A method of foot care comprising steps of:
    A) providing a container having a porous mat;

B) placing a user's foot on the porous mat;

C) placing foot-care powder on the user's foot;

D) catching any powder that falls off the user's foot during said step of placing foot-care powder on the user's foot in the mat;

E) applying powder to the bottom of the user's foot using the mat;

F) placing a flexible foot powder-containing flexible bag on top of the mat;

G) brushing the user's foot;

H) interdigitating the flexible foot powder-containing flexible bag between all of a user÷s toes prior to placing the user's foot on the mat;

I) using the flexible bag as that bag is being interdigitated between the user's toes to scrape dead skin off of the user's foot and from between the user's toes; and J) attaching the flexible bag to the user's foot after the bag has been interdigitated between the user's toes by winding the flexible bag around the user's first and last toe and attaching the ends of the bag together.

15. The method defined in claim 14 wherein the flexible bag is placed on top of the mat prior to placing the user's foot on the mat.

16. The method defined in claim 15 further including a step of placing powder in the bag before the bag is placed on top of the mat.

17. The method defined in claim 15 further including a step of scraping dead skin off of the user's foot and from between the user's toes.

18. The method defined in claim 17 wherein said scraping step includes scraping between the user's toes using the flexible bag as that bag is being interdigitated between the user's toes.

19. A method of foot care comprising steps of:

A) providing a container having a porous mat;

B) placing a user's foot on the porous mat;

C) placing foot-care powder on the user's foot;

D) catching any powder that falls off the user's foot during said step of placing foot-care powder on the user's foot in the mat;

E) applying powder to the bottom of the user's foot using the mat;

F) placing a flexible foot powder-containing flexible bag on top of the mat;

G) brushing the user's foot;

H) interdigitating the flexible foot powder-containing flexible bag between all of a user's toes; and I) attaching the flexible bag to the user's foot after the bag has been interdigitated between the user's toes by winding the flexible bag around the user's first and last toe of the user's foot and attaching the ends of the bag together.

* * * * *